United States Patent [19]

Kiner et al.

[11] Patent Number: 5,242,419
[45] Date of Patent: Sep. 7, 1993

[54] NO STICK SYRINGE

[76] Inventors: David H. Kiner, 5120 Woodland Lakes Dr.; Louis A. Gugliotta, 5105 Woodland Lakes Dr., both of Palm Beach Gardens, Fla. 33418

[21] Appl. No.: 898,537

[22] Filed: Jun. 15, 1992

[51] Int. Cl.⁵ ............................................. A61M 5/32
[52] U.S. Cl. .................................. 604/195; 604/218; 604/241
[58] Field of Search .............. 604/110, 195, 196, 198, 604/239, 240, 241, 263, 187, 194, 218

[56] References Cited

U.S. PATENT DOCUMENTS

| 4,026,287 | 5/1977 | Haller | 604/110 |
|---|---|---|---|
| 4,675,005 | 6/1987 | DeLuccia | 604/110 |
| 4,747,830 | 5/1988 | Gloyer et al. | 604/110 |
| 4,919,652 | 4/1990 | Alter et al. | 604/110 |
| 4,978,340 | 12/1990 | Terrill et al. | 604/195 |
| 4,986,813 | 1/1991 | Blake, III et al. | 604/110 |
| 4,995,874 | 2/1991 | Strickland | 604/195 |
| 5,059,179 | 10/1991 | Quatrochi et al. | 604/110 |
| 5,112,318 | 5/1992 | Novacek et al. | 604/240 |

Primary Examiner—C. Fred Rosenbaum
Assistant Examiner—Corrine Moglione
Attorney, Agent, or Firm—Richard C. Litman

[57] ABSTRACT

A no stick syringe is formed of a barrel having internal right hand threads at each end, a plunger which supports a piston near one end, and a tapered distal end provided with a left hand thread, and a needle having a cap with an internal left hand threaded and a flange configured to engage the internal threads of the barrel. The needle is connected to the tapered end of the plunger and the needle and plunger are threaded through the top internal threads of the barrel by rotating the plunger in the counterclockwise direction. At the base of the barrel the plunger is rotated clockwise to engage a needle flange with the bottom internal threads in the barrel to form a tight seal with a barrel opening and to subsequently disengage the plunger from the needle. After the syringe is used, the plunger is reconnected with the needle and released from the bottom internal by counterclockwise rotation of the plunger. The plunger is then retracted to the top of the barrel and rotated clockwise to connect the flange with the upper internal thread until stopped by internal projections, and thereafter the plunger is disconnected from the needle, whereby the syringe may be safely disposed of.

7 Claims, 2 Drawing Sheets

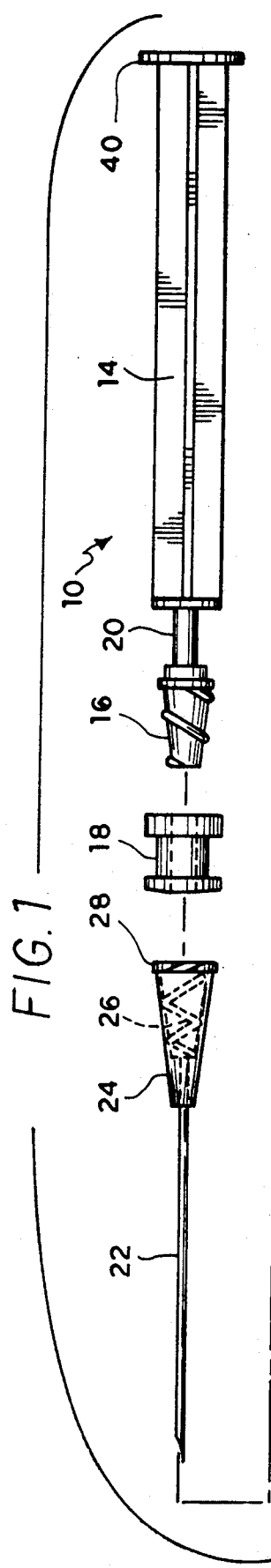
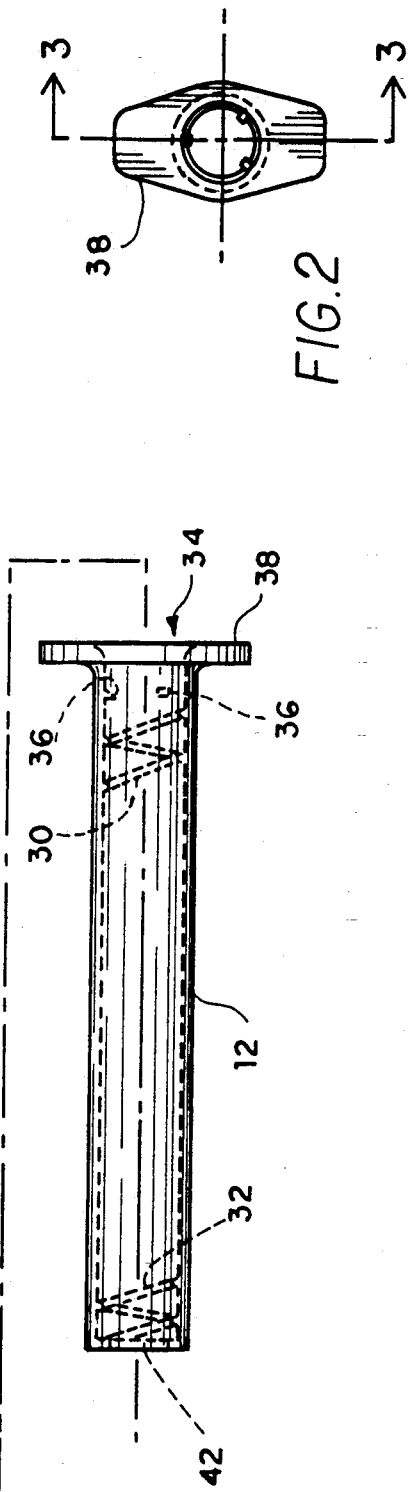
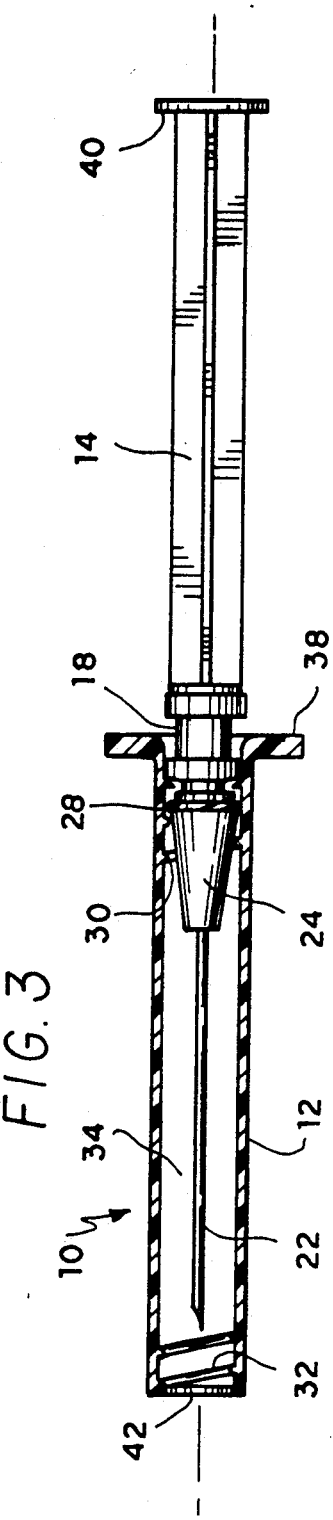

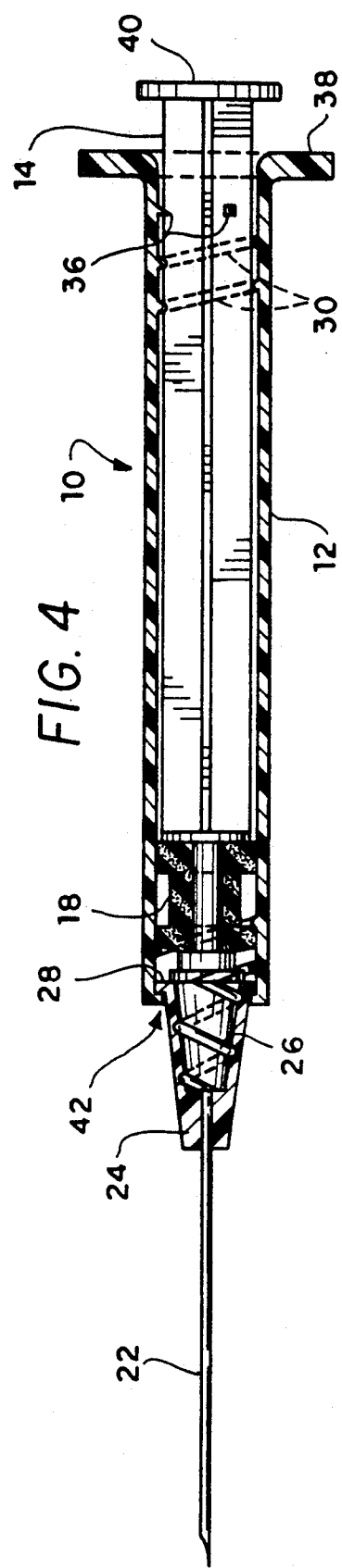
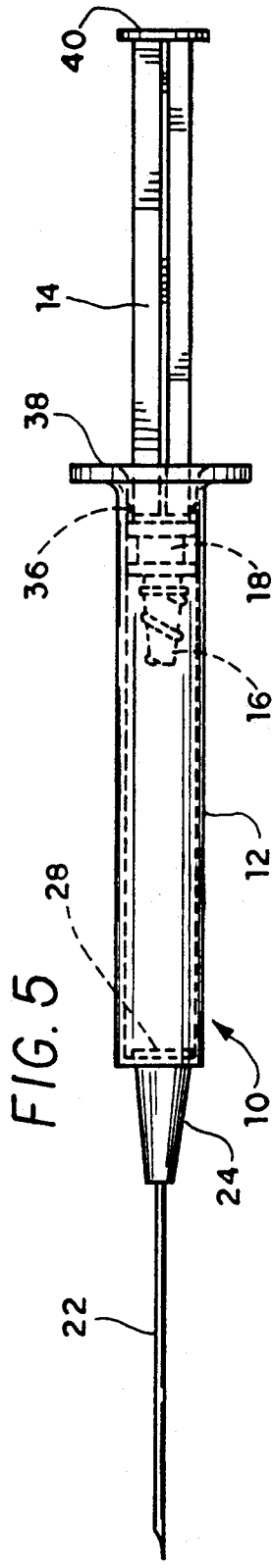
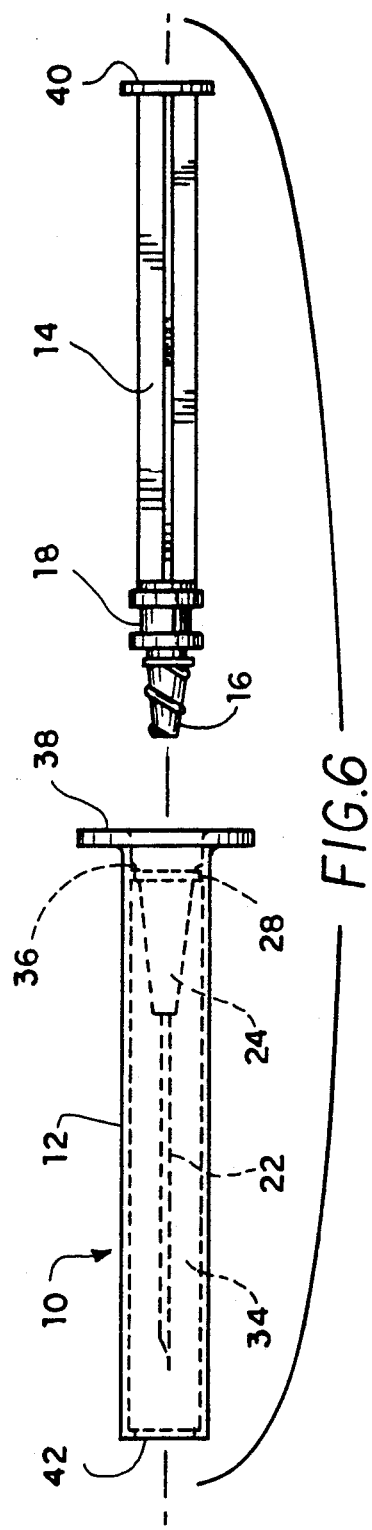

NO STICK SYRINGE

BACKGROUND OF THE INVENTION

1. Field of the Invention

This invention relates to a disposable syringe having a means for retracting the needle into a barrel after use in a manner which avoids personal contact with the needle type.

Cutaneous punctures by used needles are common occupational injuries for health care personnel. Of particular concern is the risk these workers incur of contracting a systemic disease such as Serum Hepatitis or Acquired Immunodeficiency Syndrome.

Most needle-stick injuries occur during disposal of used needles. The injury risks associated with simply recapping a hypodermic needle after use is sufficiently great for some institutions to discourage their personnel from recapping used needles.

Installing a new needle on the end of a syringe in preparation for use is generally quite safe and easy in that needles are generally packaged in solid plastic sheaths or in some other similar manner that covers the needle point until the needle is securely installed on the syringe. Thus, the plastic sheath or the like can be safely grasped and the needle can be securely affixed onto the end of the syringe, either by friction or by twisting the needle onto a "Luer" connection.

2. Description of the Related Prior Art

Disposable syringes having a means for retracting the needle into the barrel of the syringe are well known in the prior art. U.S. Pat. No. 4,026,287, issued May 31, 1977, to Irene Haller discloses a syringe having a piston 36 provided with a tapered surface which includes an engaging means formed as a thread for selective engagement with a threaded recess provided in the end wall of a barrel, the end wall supporting a needle. Subsequent to engagement between the thread and threaded recess, retraction of a plunger attached to the piston causes the end wall to break along frangible serrations so as to allow the needle to be withdrawn within the barrel. There is no disclosure in Haller of internal threads at either end of the barrel whereby the needle may be secured in either the extended position or the retracted position as desired by engagement between a flange on said needle and said internal threads.

U.S. Pat. No. 4,995,874, issued Feb. 26, 1991, to H. Allen Strickland similarly discloses a plunger 12 having a piston 14 positioned for axial movement within a cylinder 16 and having a tapered threadlock 18 engageable with a threadbore 26, whereby subsequent to engagement, needle 32 is withdrawn into the cylinder. Strickland does not disclose a cylinder having internal threads at either end provided for the purpose of securing the needle at either end of the cylinder.

SUMMARY AND OBJECTS OF THE INVENTION

The present invention comprises an elongated barrel or cylinder having internal threads at each end, a one-way stop means at the top of the barrel or cylinder arranged to enable entry of a plunger coupled to a piston and a needle mounted thereon while resisting retraction of said plunger from said barrel, said plunger carrying said piston thereon and ending in a threaded portion which engages with an internal left-hand threaded portion on the needle. The plunger, with the piston mounted thereon and the needle threadably engaged therewith, is inserted through the top of the barrel or cylinder, with the flange of the needle rotated to pass the top internal threads. The plunger, piston and needle are then pushed to the base of the barrel or cylinder until said flange engages the threads at the base of the barrel or cylinder. Clockwise rotation of the plunger serves two purposes, namely to rotate the aforesaid flange relative to the internal screw threads disposed adjacent the bottom of the barrel or cylinder to thereby attach the needle to the base of the barrel or cylinder, and thereafter to disengage the plunger from the needle whereby the plunger and piston may be withdrawn to the top of the barrel or cylinder.

Subsequent to use as a syringe, it is desirable to retract the needle into the barrel or cylinder, and to attach the needle to the barrel or cylinder in a manner to ensure that the needle tip does not extend beyond the barrel or cylinder to accidently prick the skin of a user. The plunger is depressed to the bottom of the barrel or cylinder and then rotated counterclockwise to reengage the needle with the plunger. Further rotation of the plunger in the counterclockwise direction serves to disengage the flange from the bottom internal threads, thereby enabling the plunger to be pulled to the top of the barrel or cylinder together with the needle. Clockwise rotation of the plunger enables the top flange to engage the top threads and the plunger to eventually disengage the needle, whereby the needle is now held at the top of the barrel.

An object of the invention is to enable a syringe needle to be attached at either end of a syringe barrel or cylinder.

Another object of the invention is to attach a syringe needle to a barrel or cylinder by means of a threaded connection.

A further object of the invention is to provide a means for safely and easily retracting a needle into a barrel or cylinder.

Still another object of the invention is to threadably connect a needle to a barrel or cylinder at both ends of a barrel or cylinder.

Other objects, features and advantages of this invention will become apparent from the following detailed description and the appended claims, reference being had to the accompanying drawings forming a part of the specification, wherein like reference numerals designate corresponding parts of the several views.

BRIEF DESCRIPTION OF THE DRAWINGS

FIG. 1 is a blown apart side view showing the relationship between the several elements forming the no stick syringe.

FIG. 2 is an end view of the barrel or cylinder showing the stop means preventing complete retraction of the needle from the barrel or cylinder.

FIG. 3 is a cross-sectional side view taken along line 3—3 of FIG. 2, showing the relationship between the several elements immediately following the intial insertion of the needle into the barrel, and alternatively the relationship between the several elements subsequent to needle use.

FIG. 4 is a sectional side view showing the relationship between the several elements subsequent to attaching the needle to the bottom of the barrel or cylinder.

FIG. 5 is a side view showing the relationship between the several elements subsequent to the disconnection of the plunger from the needle following the attachment of the needle to the bottom of the barrel or cylinder.

FIG. 6 shows the relationship between the several elements subsequent to the retraction of the needle into the barrel or cylinder after use and the attachment of said retracted needle to the top of the barrel of cylinder.

DETAILED DESCRIPTION OF THE PREFERRED EMBODIMENT

Before explaining in detail the present invention, it is to be understood that the invention is not limited in its application to the details of construction and arrangement of parts illustrated in the accompanying drawings, since the invention is capable of other embodiments and of being practiced or carried out in various ways. Also, it is to be understood that the phraseology and terminology employed herein is for the purpose of description and not limitation.

Shown in FIG. 1 is a no stick syringe 10 comprising a barrel or cylinder 12, a plunger 14 having a threaded end 16, a piston 18 formed of an elastomeric material such as rubber designed to be mounted on a cylindrical portion 20 of reduced diameter between the threaded end 16 and the plunger 14, and a needle 22 having a mounting cap 24 with internal threads 26 designed to mate with threaded end 16. Internal threads 26 and threaded end 16 are left-handed, such that by turning plunger 14 counterclockwise relative to needle 22, needle 22 may be attached to threaded end 16.

Mounting cap 24 has at one end a flange 28 designed to engage internal threads 30 and 32 provided at the top and bottom of barrel or cylinder 12, either by providing a mating thread on the flange 28, or by designing flange 28 to have the same pitch as provided for internal threads 30 and 32 within a bore 34. Also located internally of barrel or cylinder 12 are a plurality of one-way projections 36 which enable the plunger 14, threaded end 16, and needle 22 to be inserted manually into bore 34 as shown in FIG. 3. Piston 18 yields to bypass projections 36 and internal threads 30 and 32. By rotating plunger 14 counterclockwise, flange 28 is moved past top internal threads 30. Plunger 14 is then pushed to the bottom of barrel or cylinder 12 until flange 28 engages bottom internal threads 32, as shown in FIG. 4. By rotating plunger 14 in a clockwise direction flange 28 is threaded onto internal threads 32 to form a tight seal with opening 42. Eventually, plunger 14 is also disconnected from needle 32 which is now attached to the bottom of barrel or cylinder 12 such that plunger 14 may now be retracted to the top of barrel or cylinder 12 as shown in FIG. 5.

FIG. 2 is an end view of barrel or cylinder 12 showing the relationship between projections 36 and internal threads 30, as well as the configuration of finger rib 38 on the end of barrel or cylinder which cooperates with thumb surface 40 enabling depression of plunger 14 relative to barrel or cylinder 12.

Subsequent to use, it is desirable to retract needle 22 into barrel or cylinder 12 and further to secure needle 22 within barrel or cylinder 12 so that needle 22 cannot accidently fall through opening 42 at the bottom of barrel of cylinder 12 to thereafter accidently break the skin of the handler. To achieve this, plunger 14 is again depressed to the bottom of barrel or cylinder 12 and thereafter rotated in counterclockwise direction whereby threaded end 16 will again be connected with the internal left hand threads 26 within mounting cap 24, in a manner similar to that shown in FIG. 4. Continued rotation of plunger 14 in the counterclockwise direction will then rotate needle 22 and mounting cap flange 28 in the counterclockwise direction to disconnect flange 28 from the bottom internal threads 32. Thereafter, plunger 14 together with needle 22 may be pulled to the top of barrel or cylinder 12. Rotation of plunger 14 in the clockwise direction will first connect flange 28 to the top internal threads 30 so as to engage projections 36 and thereafter disconnect the threaded end 16 of plunger 14 from the internal left hand threads 26 within mounting cap 24. If desired plunger 14 may then be removed from the top of barrel or cylinder 12 while needle 22 remains attached to the top of barrel or cylinder 12, as shown in FIG. 6, in condition for a safe disposal.

It is contemplated that a conventional cover sheath (not shown) enclosing needle 22 will be provided during the initial step of threadably connecting threaded end 16 with the internal left hand threads 26 of mounting cap 24. Such a sheath would be removed before inserting needle 22 into the bore 34 of barrel or cylinder 12, as shown in FIG. 3.

While it will be apparent that the preferred embodiment of the invention herein disclosed is well calculated to fulfill the objects above-stated, it will be appreciated that the invention is susceptible to modification, variation and change without departing from the proper scope or fair meaning of the subjoined claims.

We claim:

1. A no stick syringe comprising:

a cylindrical barrel having a top and a bottom connected by a cylindrical bore, a finger rib located at the top of the barrel, one-way projections near the top of said barrel in said bore, an opening at the bottom of the barrel, and internal threads at each end of the barrel;

a plunger configured to slidably fit within said bore, said plunger carrying a piston and an externally threaded portion at one end; and a needle, said needle including a mounting cap and a mounting flange, said mounting flange configured to engage said internal threads at each end of the barrel, and said mounting cap including internal threads threadably engageable with said externally threaded portion of said plunger; whereby said needle may be temporarily threadably engaged with said externally threaded portion, and thereafter be threadably engaged with at least one of said internal threads at each end of the barrel;

said one-way projections enabling entry of said plunger, piston and needle into said barrel through the top thereof while preventing subsequent retraction of said needle from said barrel through said top.

2. A no stick syringe as in claim 1, wherein:

said plunger includes a cylindrical portion of reduced diameter located between said threaded end and said plunger;

said piston being of elastomeric material and located on said reduced diameter cylindrical portion.

3. A no stick syringe as in claim 2, wherein:

said internal threads at each end of said barrel are right hand threads, and the mounting cap internal threads and externally threaded portion each include left hand threads.

4. A no stick syringe as in claim 1, wherein:

said internal threads at each end of said barrel are right hand threads, and the mounting cap internal threads and externally threaded portion each include left hand threads.

5. A no stick syringe as in claim 1, said piston being of elastomeric material; whereby when said needle is withdrawn after use into said barrel and theadably engaged with the internal threads at the top of said barrel, said internal threads of said mounting cap and said externally threaded portion of said plunger may be disengaged to enable said plunger and said piston to be removed from said barrel through the top thereof while said one-way projections prevent removal of said needle.

6. In a no stick syringe which includes a barrel having internal threads at each end, a plunger, a piston mounted on the plunger, a tapered externally threaded portion at the distal end of said plunger, and a needle having an internally threaded cap portion and an external flange, the method of mounting said needle within said barrel in both an extended and a retracted position, comprising the steps of:

a) providing said internal threads within said barrel as right hand threads;

b) providing said tapered externally threaded portion and said internally threaded cap portion as left hand threads;

c) connecting said needle to said plunger by rotating said plunger in a counterclockwise direction relative to said needle, thereby threading said tapered externally threaded portion at the distal end of said plunger into said internally threaded cap portion of said needle;

d) inserting said needle and said plunger into said barrel by a combination of pushing on said plunger to move said piston past said internal threads at one end of said barrel and rotating said plunger in the counterclockwise direction to thread said flange past said internal threads at said one end of said barrel;

e) pushing said plunger and said needle to a bottom end of said barrel so as to pass said needle through an opening at the bottom end of said barrel;

f) rotating said plunger in a clockwise direction whereby said flange is rotated in a clockwise direction through said internal threads so as to form a tight seal against said bottom opening of said barrel;

g) further rotating said plunger in the clockwise direction to thereby disconnect said plunger from said seal; and h) retracting said plunger toward said one end of said barrel; whereby said needle is securely connected to the bottom end of said barrel.

7. A method as in claim 9, further comprising the steps of:

i) subsequent to the use of the no stick syringe the plunger is again pushed to the bottom of said barrel and again rotated in a counterclockwise direction to connect said tapered externally threaded portion at the distal end of said plunger with said internally threaded cap portion of said needle;

j) further rotating the plunger in the counterclockwise direction so as to disconnect the flange of said cap portion from said internal threads at the bottom of said barrel;

k) retracting the plunger and the connected needle to the top of the barrel;

l) rotating said plunger in a clockwise direction to engage the flange with the internal threads at said one end of said barrel until said flange engages one way internally directed projections at said one end of said barrel; and m) further rotating said plunger in a clockwise direction to disconnect said tapered externally threaded portion at the distal end of said plunger from said internally threaded cap portion of said needle; whereby said plunger may be removed from said syringe and said needle is connected to said one end of said barrel within said barrel, enabling the safe disposal of said syringe.

* * * * *